United States Patent
Anderson et al.

(10) Patent No.: US 10,321,982 B2
(45) Date of Patent: Jun. 18, 2019

(54) INTRA RECTAL/VAGINAL APPLICATOR TECHNOLOGY

(71) Applicant: Mark L. Anderson, Spring Valley, WI (US)

(72) Inventors: Mark L. Anderson, Spring Valley, WI (US); Christina M. Schoeder, Elmwood, WI (US)

(73) Assignee: Mark L. Anderson, Spring Valley, WI (US)

( * ) Notice: Subject to any disclaimer, the term of this patent is extended or adjusted under 35 U.S.C. 154(b) by 0 days.

(21) Appl. No.: 13/856,954

(22) Filed: Apr. 4, 2013

(65) Prior Publication Data

US 2014/0135735 A1    May 15, 2014

Related U.S. Application Data

(60) Provisional application No. 61/620,760, filed on Apr. 5, 2012.

(51) Int. Cl.
*A61D 7/00* (2006.01)
*A61M 3/02* (2006.01)
*A61M 31/00* (2006.01)

(52) U.S. Cl.
CPC ............ *A61D 7/00* (2013.01); *A61M 3/0279* (2013.01); *A61M 31/00* (2013.01); *A61M 2210/1067* (2013.01); *A61M 2210/1475* (2013.01)

(58) Field of Classification Search
CPC ...... A61M 11/00; B05B 11/0005; A61D 7/00; A61D 19/027; A61D 19/02; A61D 19/00
See application file for complete search history.

(56) References Cited

U.S. PATENT DOCUMENTS

| | | | |
|---|---|---|---|
| 693,358 A * | 2/1902 | Westlake | 604/39 |
| 901,376 A * | 10/1908 | Roberts | A61H 23/04 601/148 |
| 1,098,220 A * | 5/1914 | Borsody | 604/279 |
| 1,413,789 A * | 4/1922 | Van Schaff | A61M 29/02 601/148 |
| 2,087,511 A * | 7/1937 | Gould | 604/279 |
| 2,139,653 A * | 12/1938 | Belfrage | 604/39 |
| 2,596,597 A * | 5/1952 | Raymond et al. | 604/279 |
| 3,050,060 A * | 8/1962 | Hoffman | A61B 17/43 600/35 |
| 3,380,453 A * | 4/1968 | Leveille | A61D 19/027 604/217 |
| 3,822,702 A * | 7/1974 | Bolduc et al. | 128/831 |
| 3,938,504 A * | 2/1976 | Dickinson, III | A61B 5/1076 33/512 |
| 4,136,695 A * | 1/1979 | Dafoe | 128/831 |
| 4,236,520 A * | 12/1980 | Anderson | 604/264 |
| 4,287,888 A * | 9/1981 | Schwarz | A61H 19/34 604/150 |
| 4,301,798 A | 11/1981 | Anderson | |

(Continued)

*Primary Examiner* — Scott J Medway
(74) *Attorney, Agent, or Firm* — Skinner and Associates; Joel Skinner

(57) ABSTRACT

An applicator for use in the veterinary medical field for spraying vaccines and other medicaments, biologicals or other liquids and compositions intra-rectally. The applicator has an elongated, hollow tubular body with a connector at its proximal end for connection to a fluid supply and a curved distal end tip with a pair of apertures for dispersing fluid by spraying action.

13 Claims, 2 Drawing Sheets

(56) References Cited

U.S. PATENT DOCUMENTS

| | | | | |
|---|---|---|---|---|
| 4,329,990 | A | * | 5/1982 | Sneider ............... 604/2 |
| 4,336,801 | A | * | 6/1982 | Sentell et al. ............ 604/31 |
| 4,416,660 | A | * | 11/1983 | Dafoe ............ A61F 6/225 |
| | | | | 604/515 |
| 4,700,701 | A | * | 10/1987 | Montaldi ............ 606/28 |
| 4,701,164 | A | * | 10/1987 | Cassou et al. ............ 604/218 |
| 4,790,814 | A | * | 12/1988 | Fischl ............ A61B 17/43 |
| | | | | 600/35 |
| 4,795,438 | A | * | 1/1989 | Kensey et al. ............ 604/22 |
| 5,354,279 | A | * | 10/1994 | Hofling ............ 604/164.12 |
| 5,496,272 | A | * | 3/1996 | Chung et al. ............ 604/515 |
| 5,857,991 | A | | 1/1999 | Grothoff et al. |
| 5,899,848 | A | * | 5/1999 | Haubrich ............ 600/35 |
| 5,935,137 | A | * | 8/1999 | Saadat et al. ............ 606/135 |
| 6,726,619 | B2 | * | 4/2004 | Gil Pascual ............ 600/35 |
| 6,860,235 | B2 | * | 3/2005 | Anderson et al. ............ 119/174 |
| 8,048,101 | B2 | * | 11/2011 | Lee-Sepsick et al. ........ 606/191 |
| 8,298,187 | B2 | * | 10/2012 | Woodard et al. ........ 604/164.12 |
| 2002/0095147 | A1 | * | 7/2002 | Shadduck ........ A61B 17/22022 |
| | | | | 606/41 |
| 2002/0156420 | A1 | | 10/2002 | Anderson et al. |
| 2003/0075168 | A2 | | 4/2003 | Alchas |
| 2015/0320444 | A1 | * | 11/2015 | Brown ............ A61D 19/027 |
| | | | | 600/35 |

\* cited by examiner

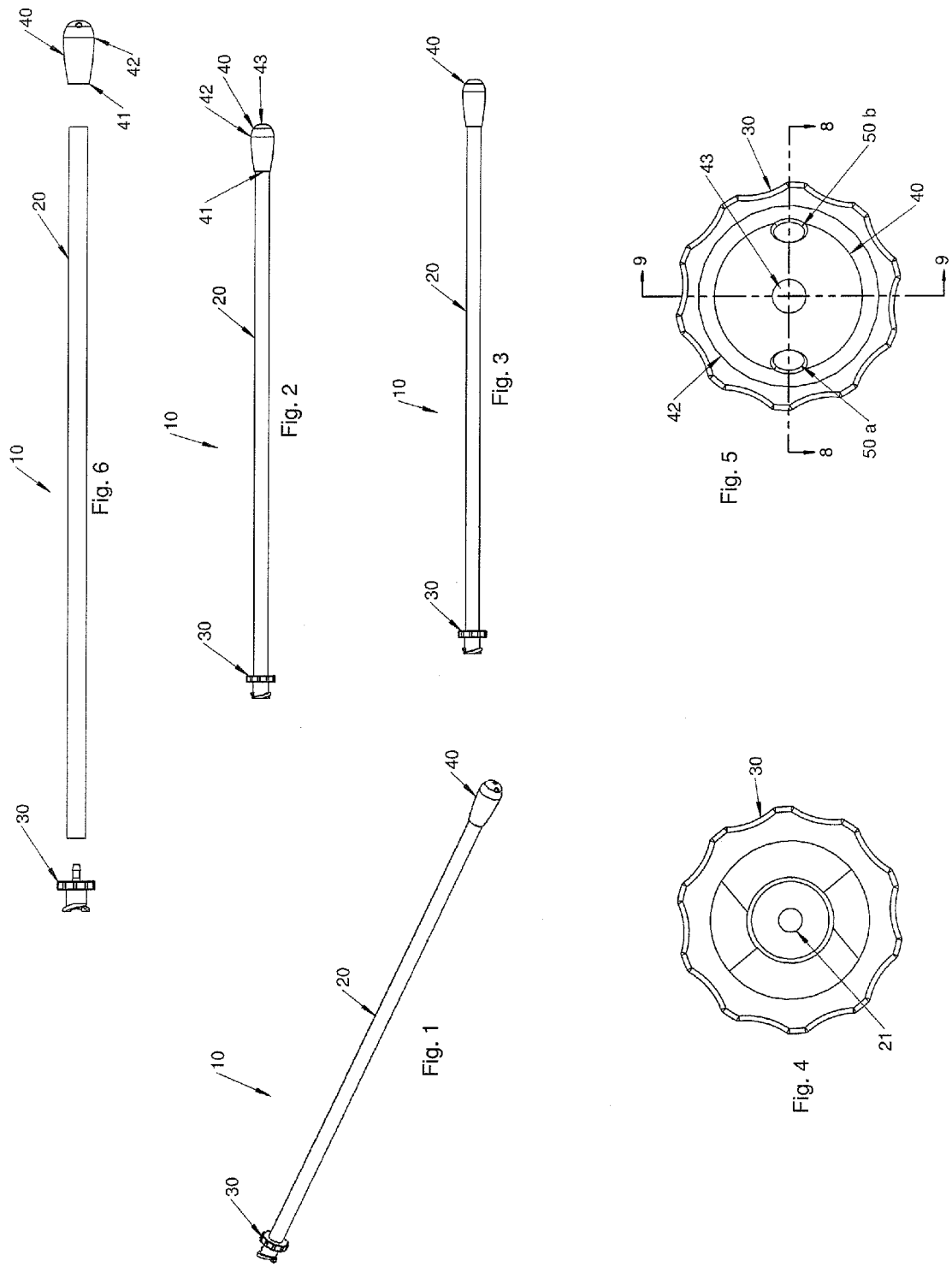

INTRA RECTAL/VAGINAL APPLICATOR TECHNOLOGY

CROSS REFERENCE TO RELATED APPLICATIONS, IF ANY

This application claims the benefit under 35 U.S.C. § 119(e) of U.S. Provisional Patent Application Ser. No. 61/620,760, filed Apr. 5, 2012, which is hereby incorporated by reference.

37 C.F.R. § 1.71(E) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

Field of the Invention

The present invention relates, generally, to human and veterinary medical systems, apparatus and methods. Particularly, the invention relates to an applicator for delivering medicaments, vaccines, biologicals and other fluids, liquids and semi-liquid materials and compositions to rectal, vaginal and other internal tissues and body cavities. The invention is particularly useful for veterinary medical applications.

Background Information

Existing technology in this field is believed to have significant limitations and shortcomings.

All US patents and patent applications, and all other published documents mentioned anywhere in this application are incorporated by reference in their entirety.

BRIEF SUMMARY OF THE INVENTION

The present invention provides an applicator apparatus and methods which are practical, reliable, easy to use, accurate, effective, and safe, and which are believed to constitute an improvement over the background technology.

The present invention is believed to involve novel elements, combined in novel ways to yield more than predictable results. The problems solved by the invention were not fully recognized in the prior art.

In one aspect, the present invention provides an applicator for use in the veterinary medical field for delivering fluids and fluid compositions such as medicaments, vaccines or biologicals, intra-rectally, intra-vaginally or to other body areas, portions and cavities. The applicator has an elongated, hollow tubular body with a connector at its proximal end for connection to a fluid supply and a curved distal end with a pair of apertures for dispersing fluid. The applicator may apply or deliver fluids by a spraying or injecting action.

In another aspect, the invention provides an apparatus for delivering fluids and fluid compositions to a patient comprising, a tubular body having a lumen for communication of fluid there through, a proximal end for connection to a supply of fluid and a distal end for contact with a patient; a connector disposed at the proximal end of the body for communicative connection with a supply of fluid, and a tip disposed at the distal end of the body for contact with the patient's body, the tip having at least one fluid exit orifice communicatively connected to the body lumen for egress of fluid from the apparatus to the patient body.

In another aspect, the invention provides a veterinary medical intra-rectal spray apparatus for delivering fluids and fluid compositions to an animal patient comprising:
  a. a semi-rigid, flexible tubular body having a lumen for communication of fluid there through, a proximal end for connection to a supply of fluid and a distal end for contact with a patient;
  b. a connector disposed at the proximal end of the body for communicative connection with a supply of fluid in a syringe, and
  c. a curvilinear tip disposed at the distal end of the body for intra-rectal communication with the patient's body, the tip having two fluid spray orifices communicatively connected to the body lumen for spray egress of fluid from the apparatus to the patient body, wherein:
    i. the tip curvilinear geometry includes a minimum circumferential diameter at the tip proximal end, the outside diameter then increasing outwardly and curvilinearly to a maximum circumferential diameter point, and the outside diameter then decreasing inwardly and curvilinearly to a distal end of the tip, and
    ii. the tip has an interior configuration comprising a proximal first section which mates with the distal end of the body, a second section which extends distally and inwardly with respect to the first section, a third section extending distally from the second section, and a distal fourth section.

And in another aspect, the invention provides a veterinary medical method of intra-rectally spraying fluids and fluid compositions to an animal patient comprising the steps of:
  a. providing an intra-rectal spray apparatus comprising
    a. a semi-rigid, flexible tubular body having a lumen for communication of fluid there through, a proximal end for connection to a supply of fluid and a distal end for contact with a patient;
    b. a connector disposed at the proximal end of the body for communicative connection with a supply of fluid in a syringe, and
    c. a curvilinear tip disposed at the distal end of the body for intra-rectal communication the patient's body, the tip having two fluid spray orifices communicatively connected to the body lumen for spray egress of fluid from the apparatus to the patient body,
  b. connecting the connector to a syringe containing a veterinary medical fluid or composition;
  c. inserting the tip into the rectum of an animal patient and then the tubular body to a predetermined area of the animal patient's body;
  d. actuating the syringe and spraying the veterinary medical fluid or composition into the rectum of the animal patient; and
  e. withdrawing the apparatus from the animal patient.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 1 is an isometric view of the applicator.
FIG. 2 is a top view of the applicator.
FIG. 3 is a bottom view of the applicator.
FIG. 4 is a left side view of the applicator.
FIG. 5 is a right side view of the applicator.
FIG. 6 is an exploded view of the applicator.

DETAILED DESCRIPTION

Figure 7:
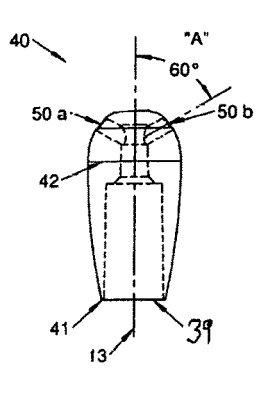
FIG. 7 is a detailed view of an embodiment of the tip of the device, showing the internal structure thereof in phantom.

FIG. 1 shows an embodiment of the applicator device 10 of the present invention. The applicator 10 is useful for delivering fluids such as gaseous, liquid, and semi-liquid medicaments, vaccines, biologicals and other compositions to patients. The applicator 10 is particularly useful for spraying fluids on rectal and vaginal orifices and tissues of animal patients such as horses, cows, pigs, sheep, goats, dogs, cats and the like. The device 10 is optimally suited for intra-rectal spraying of vaccinations in newborn and young animals such as foals with, and particularly with live bacteria vaccines.

Referring also to FIGS. 2 and 3, the applicator 10 has a thin, elongated configuration including a central body member 20 with a connector 30 disposed at its proximal end 11 and an output tip 40 disposed at its distal end 12. The applicator has a central lumen which extends from the proximal end to distal end for movement of fluid there through. The body 20 has an elongated, thin, cylindrical structure. The body 20 is preferably a tube with a central fluid passage lumen 21. The body 20 has a balance of stiffness and flexibility which permits the user to insert it longitudinally without the device 10 collapsing, but also permitting slight flexure so that the device can move around surfaces or bodies that it may encounter during insertion into the patient's body, for example curves in the rectum or vagina. The tube 20 is preferably constructed of a polymeric material such as polyvinylchloride (PVC). Preferably, the material is clear so that the operator may visualize passage of fluid in the device 10. The tube 20 material is preferably semi-rigid PVC which has a durometer reading of between 85 and 90 Shore A, and most preferably approximately 90 Shore A. The preferred tube 20 wall thickness is approximately 0.155 in. In the example embodiment shown in the drawing figures, the tube 20 has a length of approximately 8.25 inches long, with an outside diameter of approximately 0.215 inches. In this embodiment, the inside diameter of the lumen 21 of the tube 20 is approximately 0.060 inches.

Referring also to FIG. 4, the connector 30 is disposed at the proximal end and facilitates interconnection of the device 10 to a fluid supply means (not shown). In the example embodiment shown, the connector 30 is a Luer-lock style connector. The device 10 is optimally constructed and arranged to connect to a syringe containing a vaccine for intra-rectal application by a spraying action. Alternatively, the fluid supply may be a liquid reservoir (either a rigid container or a flexible bag) which is directly connected to the connector 30, or there may be an intervening tube, conduit or the like. The supply may also be or include pump, gun or other active device. The pump may be mechanical, electrical or pneumatic. The pump may be driven (by hand or electromechanically) or it may be passive, for example by gravity feed. In addition to other fluid supply sources and other types of fluids, other connectors may be useable consistent with the teachings of the invention.

Figure 8:
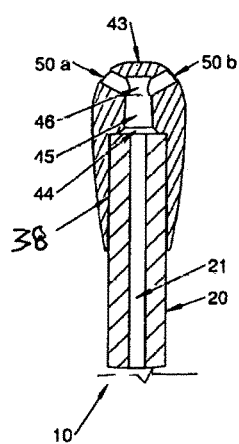
FIG. 8 is a cross-sectional view of the distal end portion of the device taken along line 8-8 of FIG. 5.
Figure 9:
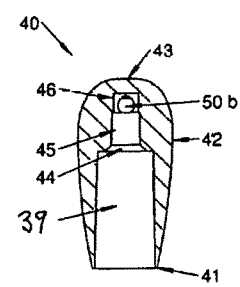
FIG. 9 is a cross-sectional view of the tip taken along line 9-9 of FIG. 5.

Referring also to FIGS. 5, 7, 8 and 9, the distal output end of the device has a tip 40 which has a curved, contoured configuration. The tip 40 has a proximal end with a proximal aperture 39 for connection with the body 20. The tip 40 geometry includes outside dimensions which vary from point 41 (also referenced in FIG. 2) where it meets the body 20, increasing slightly in a flared or outwardly tapering fashion to point (circumferentially) 42 of maximum diameter, and then decreases curvilinearly tapering inwardly to the distal end of the device 10. The tip 40 is shown to have a flat end portion 43. The tip 40 has two apertures 50 a and 50 b, which are disposed distally of the point of maximum diameter 42 and in the region where the tip 40 tapers before reaching the flat end 43. As is illustrated in FIG. 7, each aperture 50 is directed outwardly with respect to the longitudinal axis 13 of the device 10 at an angle "A". A preferred spray angle "A" is sixty (60) degrees. The apertures 50 have a diameter of approximately $\frac{1}{16}^{th}$ inches. Referring also to FIGS. 8-9, the tip 40 interior further consists of a proximal first section 38 (formed as a cylindrical sleeve extending distally from the proximal aperture 39) which mates with the distal end of the body 20, a tapered second section 44 which extends distally and inwardly with respect to the first section 38, a third section 45 (cylindrical and less than the diameter of the first section 38), and a distal fourth section 46 that preferably has an hourglass-type configuration. This interior configuration facilitates secure connection of the tip 40 to the body 20 and optimal flow of fluids through the device 10 (for example from a syringe) for application to the patient, particularly as a spray. The exterior and interior geometry is particularly well suited for intra-rectal spraying of live bacteria vaccines in newborn and young animals such as foals. In the embodiment shown, the first section 43 has a length of approximately 0.43 in. and a diameter equivalent to the outside diameter of the body 20 (0.251 in.).

This tip structure and arrangement outputs, for example by spraying, pumping or other ways, fluids such as liquids and compositions of liquids, distally and also radially. The geometry of the tip 40 facilitates passage of the device 10 into body orifices and chambers with minimal or no trauma. The exit orifice diameter and orientation projects material precisely in a desired location. And, the tip 40 geometry also facilitates withdrawal of the device 10 with minimal of no back vacuum that could cause disruption, movement, trailing or even withdrawal of projected material.

Referring to FIG. 6, the device 10 is preferably constructed of separable body 20, input connector 30 and output tip 40 components. Alternatively, these features may be constructed as a unitary structure.

The invention also provides a method of using the apparatus of the invention as follows, particularly for intra-rectal spraying. The steps of the method comprise:
  a. providing an intra-rectal spray apparatus comprising:
    i. a semi-rigid, flexible tubular body having a lumen for communication of fluid there through, a proximal end for connection to a supply of fluid and a distal end for contact with a patient;

ii. a connector disposed at the proximal end of the body for communicative connection with a supply of fluid in a syringe, and iii. a curvilinear tip disposed at the distal end of the body for intra-rectal communication with the patient's body, the tip having two fluid spray orifices communicatively connected to the body lumen for spray egress of fluid from the apparatus to the patient body, b. connecting the connector to a syringe containing a veterinary medical fluid or composition;

c. inserting the tip into the rectum of an animal patient and then the tubular body to a predetermined area of the animal patient's body;

d. actuating the syringe and spraying the veterinary medical fluid or composition into the rectum of the animal patient; and e. withdrawing the apparatus from the animal patient.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An apparatus for delivering fluids and fluid compositions intra-rectally or intra-vaginally, by spray, to a patient comprising, a tubular body having a lumen for communication of fluid there through, a proximal end for connection to a supply of fluid and a distal end for contact with a patient; a connector disposed at the proximal end of the body for communicative connection with a supply of fluid, and a tip disposed at the distal end of the body for contact with the patient's body, the tip having at least two, circumferentially oriented fluid exit orifices communicatively connected to the body lumen for egress of fluid from the apparatus to the patient body, wherein the tip has a proximal end with a proximal aperture for connection with the distal end of the body, wherein the tip has a curvilinear exterior configuration, and wherein the exterior tip curvilinear configuration includes a first circumferential diameter at the proximal edge of the tip proximal end, the outside diameter then increasing outwardly and curvilinearly toward a distal end of the tip to a second circumferential diameter point that is greater than the first circumferential diameter, and the outside diameter then decreasing inwardly and curvilinearly toward the distal end of the tip to a third circumferential diameter point at distal end of the tip, the third circumferential diameter point being less than the second circumferential diameter point, and wherein the tip has an end wall at the distal end that has a flat exterior surface, the end wall forming a distal block of fluid communicated in the body lumen thereby directing fluid circumferentially to the exit orifices, and whereby the tip is adapted to facilitate both insertion and withdrawal intra-rectally or intra-vaginally, and wherein the interior tip configuration includes a proximal first section which mates with the distal end of the body, a second section which extends distally with respect to the first section, a third section extending distally from the second section, and a distal fourth section extending from the third section, and that is communicatively connected with the at least two fluid exit orifices, and wherein the interior proximal first section has a cylindrical shape, the second section is tapered distally and inwardly with respect to the first section, the third section has a cylindrical shape, and the distal fourth section has an hourglass-type configuration when viewed cross-sectionally and longitudinally.

2. The apparatus of claim 1, wherein the apparatus is adapted for veterinary medical use with animals including horses, cows, pigs, sheep, goats, dogs, and cats.

3. The apparatus of claim 1 wherein the body is constructed of a semi-rigid polymeric material, whereby in use the body is adapted to be flexed to follow a curvilinear path and is adapted to be longitudinally inserted without collapsing the lumen.

4. The apparatus of claim 3, wherein the body is constructed of semi-rigid PVC having durometer of between 85 and 90 Shore A, and wherein the body has a wall thickness of approximately 0.155 in.

5. The apparatus of claim 4, wherein the body is approximately 8.25 inches long, has an outside diameter of approximately 0.215 inches, and has an inside diameter of approximately 0.060 inches.

6. The apparatus of claim 1, wherein the connector is a luer-type connector.

7. The apparatus of claim 1 wherein the connector is adapted to be connected to a syringe supply of fluid.

8. The apparatus of claim 7, wherein the device is adapted to apply liquid and semi-liquid vaccines.

9. The apparatus of claim 8, wherein the device is adapted to apply the vaccine by spray, intra-rectally, to a patient.

10. The apparatus of claim 1, wherein the exterior second circumferential diameter point has a maximum tip circumferential diameter, and the exterior third circumferential diameter point has a minimum tip circumferential diameter.

11. The apparatus of claim 1, wherein each orifice having a diameter of approximately $1/16$ inch, and wherein each fluid egress orifice is disposed at an approximately 60 degree angle with respect to the central longitudinal axis of the apparatus.

12. A veterinary medical intra-rectal spray apparatus for delivering fluids and fluid compositions to an animal patient comprising:

a thin, elongated semi-rigid, flexible tubular body having a lumen for communication of fluid there through, a proximal end for connection to a supply of fluid and a distal end for contact with a patient, the body having a length of approximately 8.25 inches and an outside diameter of approximately 0.215 inches;

a connector disposed at the proximal end of the body for communicative connection with a supply of fluid in a syringe, and a curvilinear tip disposed at the distal end of the body for intra-rectal communication with the patient's body, the tip having two fluid spray orifices communicatively connected to the body lumen for spray egress of fluid from the, apparatus to the patient body, the fluid spray orifices each having a diameter of approximately 0.0625 inches and being disposed in opposing directions, wherein:

the tip curvilinear exterior geometry consists of a first circumferential diameter at the proximal edge of the tip proximal end, the outside diameter then increasing outwardly and curvilinearly toward a distal end of the tip to a second circumferential diameter greater than the first circumferential diameter, and the outside diameter then decreasing inwardly and curvilinearly to the distal end of the tip which has a third circumferential diameter less than the second circumferential diameter, the end wall forming a distal block of fluid communicated in the body lumen thereby directing fluid circumferentially to the exit orifices, the distal end of the tip having a flat exterior surface with no aperture, and the tip has an interior configuration comprising consisting of a proximal first section which mates with the distal end of the body, the first section having a cylindrical shape, a second section which extends distally and inwardly with respect to the first section, the second section being tapered distally and inwardly with respect to the first section, a third section extending distally from the second section, the third section having a cylindrical shape, and a distal fourth section, extending from the third section, and which is communicatively connected to the fluid spray orifices, the fourth section having an hourglass-type configuration when viewed cross-sectionally and longitudinally, and wherein the spray orifices are disposed at an approximately 60 degree angle with respect to the central longitudinal axis of the apparatus, the interior configuration of the tip optimizing fluid flow as a spray, whereby the tip is adapted to facilitate both intra-rectal insertion distally and flexing radially with minimal or no trauma and without collapsing the tubular body lumen and intra-rectal withdrawal with minimal or no back vacuum that could cause disruption, movement, trailing or withdrawal of material sprayed by the apparatus.

13. A veterinary medical method of intra-rectally spraying fluids and fluid compositions to an animal patient comprising the steps of:

providing an intra-rectal spray apparatus comprising:

a semi-rigid, flexible tubular body having a lumen for communication of fluid there through, a proximal end for connection to a supply of fluid and a distal end for contact with a patient;

a connector disposed at the proximal end of the body for communicative connection with a supply of fluid in a syringe, and a tip having an exterior curvilinear configuration, disposed at the distal end of the body for intra-rectal communication with the patient's body, the tip having two fluid spray orifices communicatively connected to the body lumen for spray egress of fluid from the apparatus to the patient body, wherein the tip has a proximal end with a proximal aperture for connection with the body, wherein the tip has a curvilinear configuration, and wherein the exterior tip curvilinear configuration includes a first circumferential diameter at the proximal edge of the tip proximal end, the outside diameter then increasing outwardly and curvilinearly toward a distal end of the tip to a second circumferential diameter point that is greater than the first circumferential diameter, and the outside diameter then decreasing inwardly and curvilinearly toward the distal end of the tip to a third circumferential diameter point at distal end of the tip, the third circumferential diameter point being less than the second circumferential diameter point, wherein the tip has an end wall at the distal end that has a flat surface, the end wall forming a distal block of fluid communicated in the body lumen thereby directing fluid circumferentially to the exit orifices, and wherein the interior tip configuration includes a proximal first section which mates with the distal end of the body, a second section which extends distally with respect to the first section, a third section extending distally from the second section, and a distal fourth section extending from the third section, and that is communicatively connected with the at least two fluid exit orifices, and wherein the interior proximal first section has a cylindrical shape, the second section is tapered distally and inwardly with respect to the first section, the third section has a cylindrical shape, and the distal fourth section has an hourglass-type configuration when viewed cross-sectionally and longitudinally, connecting the connector to a syringe containing a veterinary medical fluid or composition; c. inserting the tip into the rectum of an animal patient and then the tubular body to a predetermined area of the animal patient's body, whereby the tip is adapted to facilitate intra-rectal insertion;

actuating the syringe and spraying the veterinary medical fluid or composition into the rectum of the animal patient; and withdrawing the apparatus from the animal patient, whereby the tip is adapted to facilitate intra-rectal withdrawal.

* * * * *